(12) United States Patent
Gentelia et al.

(10) Patent No.: US 6,511,479 B2
(45) Date of Patent: Jan. 28, 2003

(54) ELECTROSURGICAL BLADE HAVING DIRECTLY ADHERED UNIFORM COATING OF SILICONE RELEASE MATERIAL AND METHOD OF MANUFACTURING SAME

(75) Inventors: John S. Gentelia, Madison, NY (US); Ronald P. Karpowich, Frankfort, NY (US); William P. Zobrist, Lockport, NY (US); Angel R. Rodriguez, North Tonawanda, NY (US); Alexander F. Robb, Lockport, NY (US)

(73) Assignee: ConMed Corporation, Utica, NY (US)

( * ) Notice: Subject to any disclaimer, the term of this patent is extended or adjusted under 35 U.S.C. 154(b) by 146 days.

(21) Appl. No.: 09/794,676

(22) Filed: Feb. 27, 2001

(65) Prior Publication Data

US 2001/0031964 A1 Oct. 18, 2001

Related U.S. Application Data

(60) Provisional application No. 60/185,314, filed on Feb. 28, 2000, and provisional application No. 60/185,419, filed on Feb. 28, 2000.

(51) Int. Cl.[7] ............................................... A61B 18/14
(52) U.S. Cl. ............................... 606/45; 606/39; 606/41
(58) Field of Search ................................ 606/45, 39–41, 606/50, 27–29; 427/2.28, 318, 327; 607/100–102

(56) References Cited

U.S. PATENT DOCUMENTS

| | | |
|---|---|---|
| 2,102,270 A | 12/1937 | Hyams |
| 2,808,833 A | 10/1957 | August |
| 3,243,321 A * | 3/1966 | Rowand ..................... 427/327 |
| 3,336,916 A | 8/1967 | Edlich |
| 3,754,329 A | 8/1973 | Lane |
| 3,964,487 A | 6/1976 | Judson |
| 3,970,088 A | 7/1976 | Morrison |
| 3,980,085 A | 9/1976 | Ikuno |
| 4,012,551 A | 3/1977 | Bogaty et al. |
| 4,043,342 A | 8/1977 | Morrison, Jr. |
| 4,074,718 A | 2/1978 | Morrison, Jr. |
| 4,087,878 A | 5/1978 | Grieshaber et al. |
| 4,092,986 A | 6/1978 | Schneiderman |
| 4,100,309 A | 7/1978 | Micklus et al. |
| 4,126,137 A | 11/1978 | Archibald |
| 4,161,950 A | 7/1979 | Doss et al. |
| 4,188,927 A | 2/1980 | Harris |
| 4,234,972 A * | 11/1980 | Hench et al. ................ 606/70 |
| 4,314,559 A | 2/1982 | Allen |
| 4,321,926 A | 3/1982 | Roge |

(List continued on next page.)

FOREIGN PATENT DOCUMENTS

| | | |
|---|---|---|
| AU | 637755 | 11/1992 |
| EP | 225125 | 6/1987 |
| EP | 0336742 | 11/1989 |
| EP | 0479482 | 9/1991 |
| FR | 2594322 | 8/1987 |
| GB | 2060397 | 5/1981 |
| WO | 95/19739 | 7/1995 |
| WO | 96/20652 | 7/1996 |
| WO | 97/10764 | 3/1997 |
| WO | 97/11648 | 4/1997 |
| WO | 97/11649 | 4/1997 |

OTHER PUBLICATIONS

Silicones, 2 pages.
HumiSeal Protective Coatings, HumiSeal 1C53, 9 pages.

Primary Examiner—John A. Jeffery
(74) Attorney, Agent, or Firm—John R. Ley (57) ABSTRACT

A stainless steel electrosurgical blade has a single uniform layer of release material comprising substantially silicone (polysiloxane) applied directly onto the stainless steel blade portion without the necessity of one or more coatings of primer material(s), or multiple layering of the release material or mechanical roughening of the metallic blade body. Adherence of the release coating is achieved by thermally oxidizing the blade body, after cleaning it. The uniform layer is created by dipping the blade body. The release material is preferably thermally cured and non-blooming.

36 Claims, 4 Drawing Sheets

U.S. PATENT DOCUMENTS

| | | |
|---|---|---|
| 4,333,467 A | 6/1982 | Domicone |
| 4,372,315 A | 2/1983 | Shapiro et al. |
| 4,411,657 A | 10/1983 | Galindo |
| 4,481,057 A | 11/1984 | Beard |
| 4,485,810 A | 12/1984 | Beard |
| 4,492,231 A | 1/1985 | Auth |
| 4,517,975 A | 5/1985 | Garito et al. |
| 4,547,923 A | 10/1985 | DeVries et al. |
| 4,590,934 A | 5/1986 | Malis et al. |
| 4,622,966 A | 11/1986 | Beard |
| 4,658,819 A | 4/1987 | Harris et al. |
| 4,658,820 A | 4/1987 | Klicek |
| 4,704,760 A | 11/1987 | Grieshaber |
| 4,719,065 A | 1/1988 | Gibbon |
| 4,727,874 A | 3/1988 | Bowers et al. |
| 4,752,983 A | 6/1988 | Grieshaber |
| 4,770,067 A | 9/1988 | Liu et al. |
| 4,785,807 A | 11/1988 | Blanch |
| 4,848,337 A | 7/1989 | Shaw et al. |
| 4,852,200 A | 8/1989 | Phillips et al. |
| 4,876,110 A | 10/1989 | Blanch |
| 4,919,129 A | 4/1990 | Weber, Jr. et al. |
| 4,925,516 A | 5/1990 | Phillips et al. |
| 5,016,401 A | 5/1991 | Mangus |
| 5,030,218 A | 7/1991 | Alexander |
| 5,100,402 A | 3/1992 | Fan |
| 5,152,762 A | 10/1992 | McElhenney |
| 5,167,658 A | 12/1992 | Ensslin |
| 5,191,670 A | 3/1993 | Lake et al. |
| 5,197,962 A | 3/1993 | Sansom et al. |
| 5,308,311 A | 5/1994 | Eggers et al. |
| 5,330,469 A | 7/1994 | Fleenor |
| 5,380,320 A | 1/1995 | Morris |
| 5,549,604 A | 8/1996 | Sutcu et al. |
| 5,562,659 A | 10/1996 | Morris |
| 5,702,387 A | 12/1997 | Arts et al. |
| 5,713,895 A | 2/1998 | Lontine et al. |
| 5,800,427 A * | 9/1998 | Zamba ................. 606/39 |
| 5,827,275 A | 10/1998 | Morris |
| 5,885,281 A | 3/1999 | Urueta |
| 6,070,444 A | 6/2000 | Lontine et al. |
| 6,139,547 A | 10/2000 | Lontine et al. |

* cited by examiner

ELECTROSURGICAL BLADE HAVING DIRECTLY ADHERED UNIFORM COATING OF SILICONE RELEASE MATERIAL AND METHOD OF MANUFACTURING SAME

CROSS-REFERENCE TO RELATED APPLICATION

This application is related to, and claims the benefit of, two previously filed U.S. provisional patent applications, titled "Electrosurgical Blade" and "Method Manufacturing and Electrosurgical Blade," application Ser. Nos. 60/185,314 and 60/185,419 respectively, both filed Feb. 28, 2000 by the present inventors.

FIELD OF THE INVENTION

This invention relates to a disposable electrosurgical blade or active electrode used to perform electrosurgical procedures and to a method manufacturing such a blade. More particularly, the present invention relates to a new and improved electrosurgical blade exhibiting release characteristics as a result of having a relatively thin and uniform cross-sectional coating of nonstick material comprising silicone which is directly adhered to and supported on a metallic body of the blade. Even more particularly, the present invention relates to a new and improved method of fabricating an electrosurgical blade having non-stick, release characteristics by steps involving adhering a nonstick coating comprising silicone to an oxide of the metal body, thereby avoiding the typical requirements for mechanically roughening the metal body to achieve adequate adhesion or for applying intermediate layers of primer materials or multiple layers of materials to attain the desired characteristics.

BACKGROUND OF THE INVENTION

In general, electrosurgery involves the application of relatively high frequency or radio frequency (RF) current to living tissue. Depending upon the characteristics of the RF signal, electrosurgery is used to cut tissue, to coagulate bleeding (hemostasis) from the tissue or to both cut and coagulate simultaneously. The typical frequency of the electrosurgical current is from approximately 400 kHz to 750 kHz, because this frequency range avoids stimulating the nervous system. The electrical power applied can vary from a few watts for delicate neurosurgical procedures to approximately 300 watts for cutting substantial tissues in open surgical procedures. The open circuit voltage prior to energy transfer into the tissue may be in the range of 5,000–10,000 volts peak to peak. Of course, the voltage drops substantially as the current flow increases through the impedance of the tissue. Typical tissue impedances range between about 10 ohms and 500 ohms.

Electrosurgery is performed by connecting the electrosurgical blade or active electrode to an electrosurgical generator, activating the generator to supply the electrosurgical waveform, and delivering the energy of the electrosurgical waveform to the tissue through the blade. The blade is positioned in a pencil-like handpiece which the surgeon manipulates to achieve the desired effect at the surgical site. Selecting and adjusting the characteristics of the electrosurgical waveform delivered by the electrosurgical generator allows the surgeon to cut the tissue, to coagulate bleeding from the tissue, or to simultaneously cut and coagulate. The ability to control the application of electrical energy to the tissue to cut and coagulate tissue is one of the substantial advantages of electrosurgery, and such advantages contribute to the use of electrosurgery in most major surgical procedures.

The physical characteristics of the typical electrosurgical blade also are used advantageously by the surgeon to accomplish different surgical procedures. The typical electrosurgical blade has an elongated working area with a shape similar to a rectangle in cross-section. Two relatively-broad and generally-parallel sides extend along and exist on opposite sides of the working area. The two broad sides are joined by a narrow edge which extends between the broad sides and which curves around a distal end or tip of the working area. The edges form the narrow legs of the cross-sectional rectangle while the broad sides form the wide legs of the cross-sectional rectangle.

Cutting is achieved by bringing the narrow edge into close adjacency with the tissue. A high current density at the narrow leading edge transfers energy into the tissue as relatively short arcs, thereby causing enough heat to explode or rupture the cells of the tissue at the interface with the narrow leading edge. The tissue separates at the leading edge leaving a well-defined incision. It is in this manner that the current from the electrosurgical blade cuts the tissue, rather than the tissue being separated from the physical contact and mechanical action of a sharp edge, as is the case with a traditional scalpel. Indeed, the narrow edge of the typical electrosurgical blade is not sharp and cannot cut tissue as a result of mechanical action. The separated tissue passes by the broad sides of the working area of the active electrode as the surgeon guides the blade, while the electrical energy creates the incision.

Coagulating bleeding surfaces usually involves bringing the tip of the working area of the blade to a point spaced slightly above the bleeding surface and delivering a duty cycle type of coagulating electrosurgical waveform. The duty cycle coagulating waveform includes an on time period during which the high frequency electrical signal is delivered, followed by an off-time during which no electrical energy is delivered. The coagulating duty cycles are repeated at a frequency in the neighborhood of approximately 30 kHz, with a power of approximately 50–80 watts. Longer arcs of electrical energy are transferred in a spray-like manner from the tip of the blade and these arcs penetrate into the tissue to create a reticulum which both activates the normal clotting mechanism in the blood and thermally seals the surface of the tissue. Bleeding vessels are coagulated in much the same manner except that the tip of the blade is sometimes placed in close adjacency with the severed vessel, causing the arcs to be concentrated at that location.

Simultaneous cutting and coagulating occurs by blending the duty cycle coagulation waveform with a continuous waveform. In general, this involves increasing the on-time of the duty cycle to sufficient amount which permits cutting to occur but which still allows coagulation to be achieved. Because of the relative convenience and quickness with which coagulation can be achieved, many surgical procedures will usually progress more rapidly by using electrosurgery than if electrosurgery was not used.

The bursting cells release cell protein and fluids into contact with the surface of the electrosurgical blade. Blood also contacts the surface of the electrosurgical blade as the tissue is severed and when the surgeon uses the electrosurgical blade to coagulate blood flow. Different types of tissues emit other types of body fluids into the surgical field, and these other body fluids may contact the electrosurgical blade.

The amount of electrical energy delivered to the tissue through the electrosurgical blade is sufficiently high so that the current flow through the blade itself heats the blade.

Since the typical tissue impedance ranges in the neighborhood of tens of ohms to a few hundreds of ohms, the impedance of the blade itself is significant enough relative to the impedance of the tissue that the blade absorbs enough of the transferred energy to increase its temperature significantly during electrosurgery. The increased temperature of the blade causes the cell fluids, body fluids and blood to dehydrate, denature and accumulate on the blade in the form of a crust-like buildup. Unless periodically removed, the crust-like buildup increases as the blade is used.

The crust-like buildup is a significant distraction to the surgeon. The crust-like material negatively affects the electrosurgical performance. The crust-like buildup spaces the blade from the tissue, thereby making it difficult or impossible to transfer energy into the tissue to achieve the desired electrosurgical effect. The crust-like buildup on the broad sides of the blade also causes the blade to drag against the tissue at the incision, thereby creating an undesirable "feel" when manipulating the instrument. The crust-like buildup may obscure the vision of the surgeon at the expected location of energy delivery from the blade into the tissue, thereby making it more difficult to achieve the precise effect desired. The problem and consequences of the crust-like buildup on electrosurgical blades has been recognized as a significant issue in electrosurgery for many years.

One approach to removing the crust-like buildup has been for the surgeon to periodically scrape the blade as clean is possible, perhaps by using scalpel or other tool to scratch the strongly-adhering, crust-like material off of the broad sides of the blade. Generally speaking, because most of the energy transfer is through the narrow edges during cutting and coagulation, this energy transfer tends to keep the narrow edges clean. Consequently, the buildup of crust-like material on the broad sides of the blade is the most significant distraction. Another approach to removing the buildup has been to use specifically-designed mechanical cleaning devices into which the surgeon could insert and withdraw the blade to scrape or otherwise clean off the buildup. The mechanical scraping and cleaning techniques are generally not preferred by surgeons because the scraping activity itself prolongs the surgical procedure. Moreover, scraping is generally not fully effective in removing all of the crust like material, but is better than no attempt to remove the buildup from the blade whatsoever. Consequently, the necessity to scrape the blade during the surgical procedure has been tolerated by surgeons.

Another approach to avoiding the crust-like buildup on electrosurgical blades has been to coat the exterior of the blades with a nonstick or release coating. The nonstick or release coating minimizes the adherence of the crust-like materials. The release coating allows the buildup to be removed more conveniently by a wiping action rather than a scraping action. The nonstick, release coating is primarily effective on the broad sides of the blade because the intense energy transfer from the narrow edges usually eliminates any coating on those surfaces after the blade is used. Since the broad sides of the blade are the primary location where the buildup normally occurs, the existence of the nonstick release coating on the broad sides achieves the primary benefit.

A variety of different types of release coating materials have been applied to electrosurgical blades, all with varying degrees of success and preference by surgeons. Among the types of release materials which have been used on electrosurgical blades are fluorinated hydrocarbon materials (similar to "Teflon"), silicone (polysiloxane), ceramic composites, and paralyene polymers, among others. These substances have been used on electrosurgical blades primarily because of their nonstick or release surface characteristics. Other factors which influence the choice of such materials for coating electrosurgical blades involve biocompatibility, heat resistance, dielectric strength, and adherence, among others.

Adherence is a particularly important characteristic, because the nonstick, release material should remain on the broad sides of the blade, despite the relatively high temperature of the metal blade and the occasional electrical arcing from the broad sides to the adjoining tissue. Because of the desire for good adherence, the typical approach has been to mechanically roughen the metal body prior to applying the release or nonstick coating. Mechanically roughening the surface of the metal body increases the surface area of the metal body by creating a large number of mechanical peak and valley aberrations into an otherwise smooth surface. The increased surface area and the texture of the peaks and valleys provides a complex mechanical structure to which the coating material will adhere with increased tenacity. Typical mechanical roughening techniques involve grit blasting, etching, burnishing, or knurling. Another roughening technique is to fuse a layer of textured material to the smooth surface. The fused textured material causes the release coating to adhere.

While the roughened surface achieves the objective of enhanced adherence of the release material, it also creates certain undesirable characteristics. Each of the peaks of the roughened surface presents a minuscule elevated point source from which an electrical field gradient exists when the metal body of the electrosurgical blade is energized with high voltage. Field gradients are responsible for initiating arcs of the electrical energy. In most circumstances, the arcs should not be initiated from the broad sides of the electrosurgical blade, but instead should be encouraged to form mostly from the narrow edge or tip of the blade. The corners where the broad sides join the narrow edges create the desirable field gradient locations for the initiation of the arcs to deliver the energy for cutting and coagulating as described above. Arcing from the points of the roughened broad sides of the blade may have the tendency to destroy the nonstick or release coating material on the broad sides by erupting the coating from the points were the arcs initiate from the peaks. Of course, destroying the nonstick coating on these broad sides diminishes or destroys the nonstick and release characteristics of the blade.

One technique of avoiding the undesirable point-source field-gradient effects of the roughened surface is to apply thick or multiple coats of release or nonstick material to the blade. Once the coating has been built up to a sufficient thickness, enough electrical insulation exists to eliminate or inhibit the arcing from the broad sides. However, applying multiple coats of material to the blade increases its manufacturing cost. The width of the blade between the coatings on the broad sides is also increased by the added width of the multiple layers of coatings. The increased width creates more drag on the adjoining tissue as the blade cuts.

Some types of nonstick or release coatings, particularly those consisting primarily of silicone (polysiloxane), have the tendency to develop hair-like fingers which extend out from the outer surface of the coating. This effect is referred to as "blooming," and appears to result from the type of silicone used and/or the techniques used to cure it, such as gamma ray or other high-energy curing techniques. The hair-like fingers may continue to grow or develop with time, after the time when the silicone coating is otherwise considered to be initially cured. Such fingers cause additional surface area and present the opportunity for the crust-like material to adhere to the coating, even though the coating material itself is a release type of coating. It may be possible that the hair-like fingers break off from the remaining coating during use of the blade.

The recognized technique of achieving adequate adherence of the release or nonstick coating is to mechanically roughen the surface of the metal blade body. Typically the metal blade body is formed of stainless-steel. After roughening the stainless-steel body, it is also typical that a primer coat the applied before the release coating is applied to the primer coat. The primer coating adheres to the roughened metal of the blade body, and the primer coating also provides a surface to which the release or nonstick coating adheres. Some types of release coating materials contain a self-priming component, such as an adhesive resin, but even using these types of materials have required roughening of the surface before their application. While this surface-roughening technique achieves adequate adherence of the release or nonstick coating, it increases the cost of manufacturing the electrosurgical blade because of the added requirements for roughening the surface and applying multiple coatings of different types of materials.

The applicants are aware of one instance where a fluorinated hydrocarbon release coating has been directly applied to the stainless-steel metal body of an electrosurgical blade without first mechanically roughening the surface. In this situation, the stainless-steel blade was thermally oxidized for the purpose of cleaning the blade body by burning off or driving off foreign substances. The fluorinated hydrocarbon material contained an inherent primer or binder which caused the fluorinated hydrocarbon coating material to adhere. The fluorinated hydrocarbon material was sprayed onto the blade, and typically resulted in a thickness of between 0.0007 to 0.0015 inches.

It is with respect to these and other background considerations that the present invention has evolved.

SUMMARY OF THE INVENTION

One aspect of the present invention relates to a stainless steel electrosurgical blade which has a single, relatively thin and uniform layer of a silicone release material applied directly onto the stainless steel blade portion without applying one or more coatings of primer materials, without applying multiple layers of the release material, or without mechanically roughening the metallic body of the active electrode. Another aspect of the invention involves achieving adequate adherence of silicone nonstick or release materials to a stainless steel body of an electrosurgical blade without the necessity of mechanically roughening the blade body. A further aspect of the invention relates to eliminating the peaks and valleys caused by mechanically roughening the sides of an electrosurgical blade, and by so doing, substantially reducing or eliminating the prospects of unintended arcing through the release coating from point source field gradients at the peaks of the roughened surface. A further aspect of the invention involves a discovery that an oxide formed from iron of a stainless steel metallic body of the active electrode is sufficient to adhere a nonstick, release material comprising substantially polysiloxane to the metallic body of the active electrode in this manner sufficient for electrosurgery. Still another significant aspect of the invention relates to manufacturing an electrosurgical blade with a nonstick, release coating comprising silicone in a more cost-effective and efficient manner.

In accordance with these and other aspects, the present invention is directed to an electrosurgical blade or active electrode used for conducting electrical energy to tissue during an electrosurgical procedure. The active electrode includes a conductive metallic body having a working area portion and a connection end to which the electrical energy is conducted. The working area portion of the body includes at least one broad side which has been oxidized. A nonstick release coating comprising substantially polysiloxane is directly adhered to the oxidized broad side of the body. The nonstick release coating has a substantially uniform cross-sectional thickness. The oxidation provides sufficient adherence for the nonstick release coating, thereby avoiding the necessity for applying primer coats, multiple coats or roughening the surface to obtain adequate adherence of the release coating. Because it is not necessary to roughen the broad side, there are no peaks and valleys to create point source field gradient effects that might cause unintended arcing through the release coating. The thickness of the coating can be made thinner because there are no peaks which must be insulated to avoid the unintended arcing. The adherence obtained by the oxidized broad surface provides adequate adherence for the release coating, and the extent of oxidation may be controlled to achieve the maximum adherence.

Also in accordance with the above noted aspects, the invention relates to a method of manufacturing a coated electrosurgical blade or active electrode from a conductive metallic body. The metallic body has a working area portion including at least one broad side having smooth and non-roughened characteristics and also has a connection end to which electrical energy is conducted when the active electrode is used in electrosurgery. The steps of the method involve oxidizing an element of the metallic body over the broad side, uniformly coating the oxidized broad side with a liquid nonstick release material containing substantially polysiloxane, and curing the polysiloxane of the material. The thin liquid coating, when cured, provides a relatively thin and uniform coating to achieve the nonstick release characteristics as described above. These improved characteristics are achieved without the complexity and expense of applying multiple coats of release material or primer material and release material, curing the material between coatings, or manipulating the electrode in complex movements to create special non-natural coating contours.

Preferable features of both the active electrode and its method of manufacture involve thermally oxidizing the broad side under circumstances where the metallic body is stainless-steel and iron in the stainless steel is oxidized into iron oxide. The extent of the iron oxide created is preferably that amount to achieve maximum adherence of the coating. The thermal oxidation is preferably achieved by heating the stainless-steel body in an oxygen containing environment. Preferably, the polysiloxane of the nonstick release material is a thermally curing polysiloxane which does not bloom hair-like fingers during or after curing. The uniformity of the coating extends transversely in cross-section with respect to the longitudinal extent of the broad side. In addition, preferable characteristics of the uniform cross-sectional coating cause it to change or increase in thickness longitudinally from a distal tip of the broad side to a location on the broad side which is more proximal from the distal tip.

The coating is preferably formed in a single layer by dipping. Preferably, the broad surface is vertically oriented to extend downward and the dipping occurs by inserting and withdrawing the broad surface vertically from a pool of the liquid nonstick release material, preferably at a controlled rate to create the uniform coating. Excess material is allowed to drip from the downward extending broad side. Thereafter, the broad side is preferably inverted to extend vertically upward. The upward extension of the coated broad side allows liquid material on the broad side to move away from a distal tip toward a location spaced proximally from the distal tip until a thickness of the substantially uniform coating increases approximately linearly along the length of the broad side from the distal tip to the location spaced proximally from the distal tip, before the polysiloxane is cured. A shank portion of the body preferably includes at least one groove formed adjacent to the working area portion to receive and contain excess liquid coating material applied to the body when the blade is inverted and to avoid having the release material coat any other undesired parts of the active electrode. The metallic body is preferably ultrasonically cleaned and passivated before oxidizing, coating and curing it.

A more complete appreciation of the present invention and its scope may be obtained from the accompanying drawings, which are briefly summarized below, from the following detail descriptions of presently preferred embodiments of the invention, and from the appended claims.

DETAILED DESCRIPTION

A single use or disposable electrosurgical active electrode or blade 100 is shown in FIGS. 1–5. The blade 100 includes a metallic blank or body 110 which has been formed in the conventional shape of a typical electrosurgical blade. The typical electrosurgical blade shape includes a distal working area portion of the 112 which has two oppositely positioned broad sides 114. Relatively narrow edges 116 connect to the broad sides 114 at corners 118. At a distal end or tip 120 of the working area 112, the broad sides 114 terminate in a somewhat curved configuration. The narrow edges 116 continue around the curved configuration at the tip 120.

The working area 112 has a single uniform layer coating 122 of nonstick, release material comprising substantially silicone (polysiloxane) initially applied over and adhered to the broad sides 114 and the narrow edges 116. Upon use of the electrosurgical electrode 100, any coating 122 initially present on the narrow edges 116 and at the corners 118 in the vicinity of the tip 120 will vaporize as a result of the heat and electrical arcing energy which is preferentially delivered from those portions of the working area 112. The coating 122 remains adhered to the broad sides 114 of the electrosurgical blade 100 even after use to provide the nonstick and release characteristics of the electrosurgical blade along the broad sides 114 where such nonstick, release characteristics are primarily desired and required.

Figure 2:
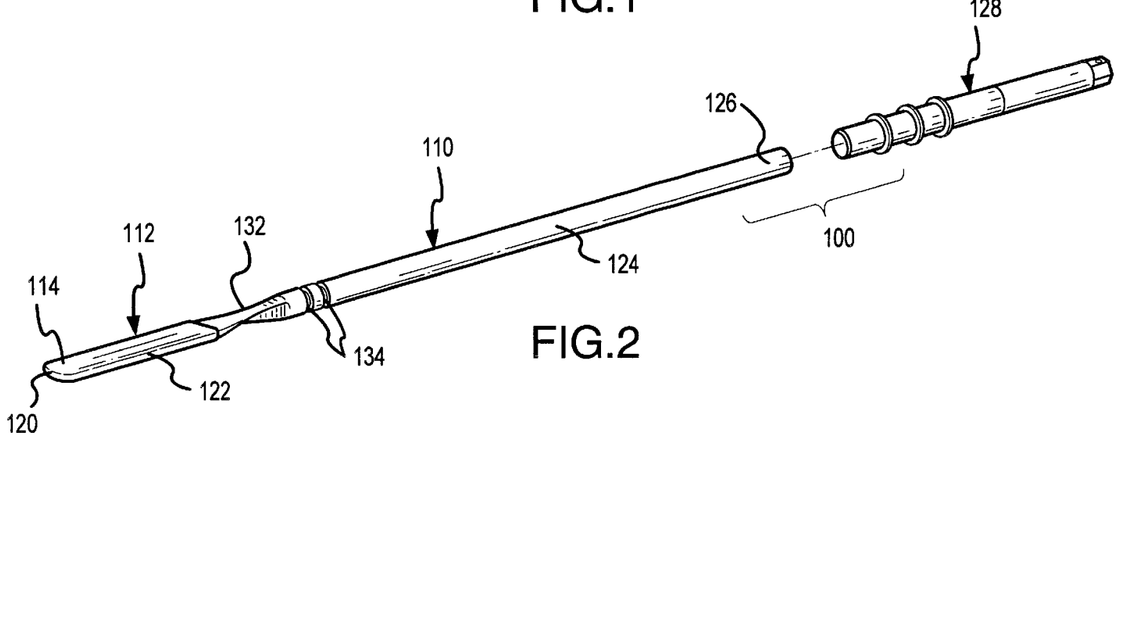
FIG. 2 is an exploded view of the electrosurgical blade shown in FIG. 1.

A cylindrically shaped proximal shank portion 124 is located at the opposite end of the blade body 110 from the working area portion 112. The shank portion 124 includes a cylindrically shaped proximal end 126 which is intended to fit within and connect to a standard collet or receptacle in a conventional electrosurgical handpiece (not shown). The surgeon holds the handpiece to manipulate the blade 100 after it has been connected to the handpiece. The collet or receptacle is electrically connected to an electrosurgical generator by conductors which extend from the handpiece to the generator (not shown). It is through this electrical connection that the electrosurgical waveform of voltage and current from the electrosurgical generator is delivered to the blade 100 and from the blade 100 into the tissue.

Figure 1:
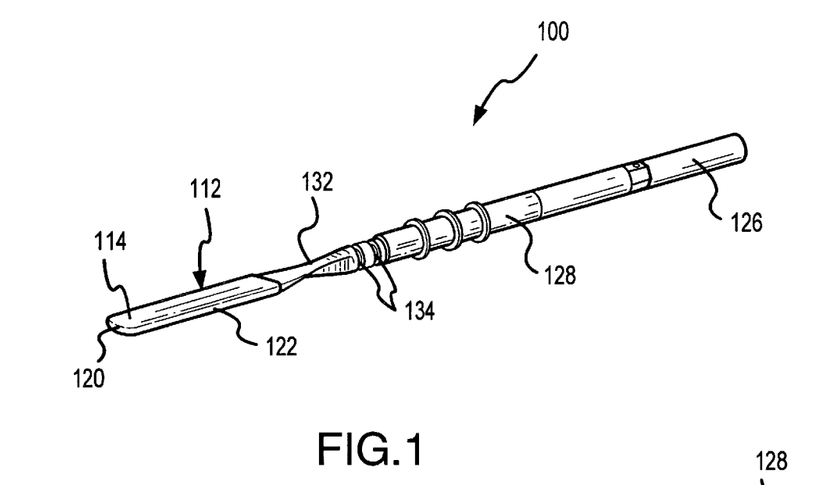
FIG. 1 is a perspective view of an electrosurgical blade incorporating the invention.

A hub 128 which is formed from electrically insulating material covers a substantial portion of the shank portion 124 but leaves the proximal end 126 exposed (FIG. 1). The exposed proximal end 126 is inserted into the collet of the handpiece (not shown), thereby connecting the electrosurgical blade to the electrosurgical generator (also not shown). The hub 128 includes a center cylindrical opening 130 which allows the hub 128 to be slipped onto the cylindrically shaped shank portion 124. The resulting frictional fit firmly and rigidly retains the hub 128 to the blade body 110. The electrical installation of the hub 128 prevents electrical shock from an inadvertent contact with the shank portion 124. The electrical insulation of the hub 128 also prevents unintended arcing to the patient tissue from the shank portion 124. The hub 128 has an exterior surface configuration which allows the electrosurgical blade 100 to be firmly gripped with finger pressure when inserting it into or removing it from the handpiece (not shown).

A neck area 132 is located between the cylindrically shaped shank portion 124 and the working area portion 112. A neck area 132 transitions between the cylindrically shaped shank portion 124 and the generally rectangularly shaped (in cross-section) working area portion 112. As is discussed below, the neck area 132 also provides a location for excess material of the coating 122 to accumulate when the coating 122 is applied to the working area portion 112. In addition and if necessary, at least one indention or concentric groove 134 is formed in the distal end of the shank portion 124 near the neck area 132. The concentric groove 134 also permits any excess material from the coating 122 to accumulate. Preventing excess material from the coating 122 from flowing onto and coating the shank portion 124 assures that the hub 128 will remain firmly connected to the shank portion 124. Preventing excess material from the coating 122 from flowing onto the proximal end 126 of the shank portion 124 also assures that the coating 122 will not inhibit the electrical connection of the end 126 into the collet of the handpiece (not shown). The grooves 134 are not part of the typical configuration of an electrosurgical blade.

Although not shown, another type of typical electrosurgical blade extends the shank portion 124 between the hub 128 and the neck area 132. This type of electrosurgical blade is typically used in tonsillectomies where it is necessary to extend the working area portion 112 a considerable distance from the handpiece. In this type of elongated electrosurgical blade, an electrically-insulating heat shrink tubing is placed over the elongated shank portion between the hub 128 and a proximal location of the working area portion 112.

Figure 4:
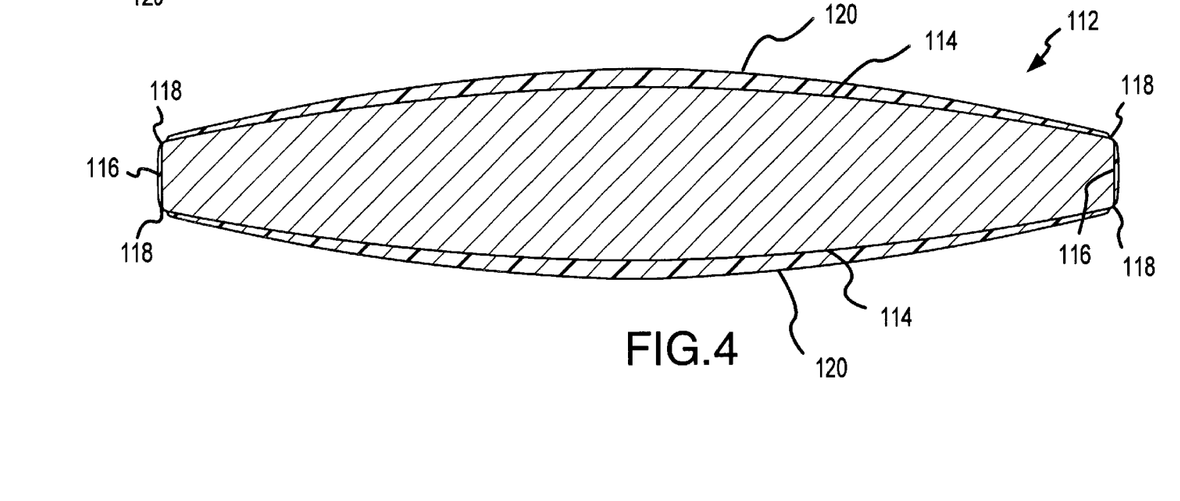
FIG. 4 is an enlarged transfers cross-sectional view of the blade body shown in FIG. 3, taken substantially in the plane of lines 4—4 of FIG. 3.

The typical configuration of the electrosurgical blade is achieved by stamping or coining the working area portion 112 and the neck area 132 from a pre-existing cylindrical segment of metal which is similar to and which extends from the cylindrically shaped shank portion 124. While the dimensions of the working area portion 112 may vary somewhat, the width of the broad sides 114 (between the edges 116) may be in the neighborhood of about 0.100 inches and the width of the narrow edges (between the broad sides 114) may range between 0.010 and 0.015 inches. The broad sides curve slightly outward in the center beyond the corners 118, as shown in FIG. 4, because of the coining process. Generally the amount of this outward curvature will be modest, in the neighborhood of approximately 0.001 and 0.009 inches between the highest center point and the corners 118. Generally, the length of the working area is between approximately 0.700 inches and 0.800 inches, although this dimension is not particularly critical since approximately only the most distal half of the working area portion 112 is typically involved in electrosurgery.

Typically the surfaces of the broad sides 114 will be substantially smooth as a result of the stamping or coining which forms the blade body 110. Because the coining or stamping involves a mechanical deformation of the metal, there will be slight aberrations in the smoothness of the broad sides 114. However, the substantially smooth broad sides 114 have not been intentionally mechanically roughened in a manner similar to the roughening that results from grit blasting, etching, burnishing, or knurling.

The coating 122 is as uniform in cross-sectional thickness (FIG. 4) as is possible over the broad sides 114 of the blade 100. The uniformity in the cross-sectional thickness of the coating 122 will vary slightly between the corners 118, as shown in FIG. 4, because the natural laws of science. The naturally-occurring effects of surface tension, increased concentration of stress which creates more fluidity or less viscosity of the liquid coating 122 before it cures at the edges, and other comparable naturally-occurring effects, cause a liquid layer of the coating 122 to pull back on itself at the corners 118, thereby reducing its thickness at those corners and for a transitional width beyond the corners 118. The coating 122 has a relatively uniform thickness in the middle areas of the broad sides 114, as shown in FIG. 4. Because the narrow edges 116 have relatively little width between the corners 118, the lesser amount of coating 122 on those edges may be somewhat more curved as a result of the natural science effects just described. The cross-sectional characteristics of the coating 122 are the most uniform available from natural physical science, without manipulating the coated blade body 110 to accumulate the coating in greater or non-uniform thicknesses beyond those available from natural science.

Figure 5:
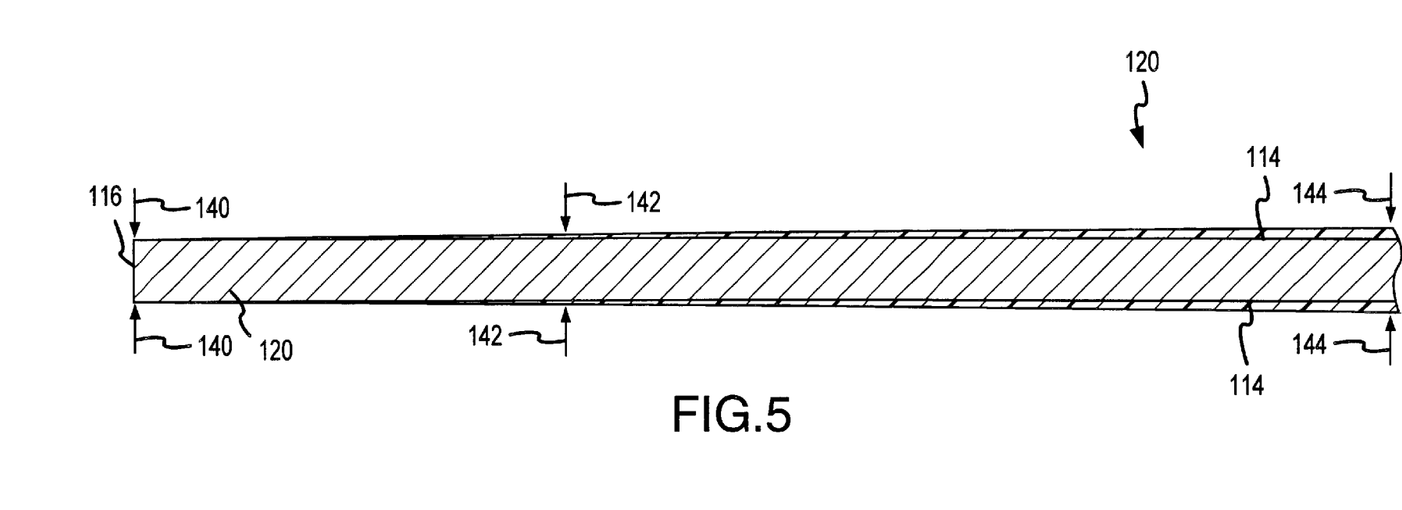
FIG. 5 is an enlarged longitudinal sectional view of the blade body shown in FIG. 3, taken substantially in the plane of lines 5—5 of FIG. 3.

In addition to the uniform cross-sectional thickness of the coating 122 transversely across the working area portion 112, as shown in FIG. 4, the uniform cross-sectional thickness increases slightly with increasing proximal distance from the distal tip 120 as shown in FIG. 5. The uniform coating 122 is the least thick near the tip 120 and the most thick at approximately a position midway between the tip 120 and the neck area 132. The maximum cross-sectional thickness of the coating at a point 140 (FIG. 5) at the distal tip 120 on the broad sides 114 is approximately 0.0004 inches. The maximum thickness of the coating at a point 142 (FIG. 5), which is approximately.125 inches approximately from the distal tip 120 on the broad sides 114, is approximately from 0.0007 to 0.0014 inches. The maximum thickness of the coating at a point 144 (FIG. 5), which is approximately 0.375 inches from the distal tip 140 on the broad sides 144, is approximately between 0.0014 to 0.0028 inches.

A thin uniform coating at the tip 120 is desired because most of the electrosurgery occurs between points 140 and 142 (FIG. 5). A thicker uniform coating is desired in the middle and proximal locations of the working area portion 112, between points 142 and 144, because the reduced amount of arcing and energy transfer in these middle and proximal locations on the working area portion 112. The manner of creating the longitudinally increasing thickness of the uniform cross-sectional coating from the tip 120 to the middle locations on the broad sides 114 of the working area portion 112 is described below in connection with the process for manufacturing the blade 100.

The coating material 122 is shown in FIGS. 1–4 as a separate layer which terminates at approximately the distal end of the working area portion 110. For the reasons just noted, the coating material 122 should cover the broad sides 114 of substantially the entire working area portion 110. In actuality, the coating 122 may extend into the neck area 132 and possibly into the concentric grooves 134, and consequently may not appear to terminate at a specific demarcation line as a shown in FIG. 14.

Because of the thin cross-sectional uniformity and the flexibility of the coating 122, the working area portion 112 may be bent up in a direction perpendicular to the broad sides 114 at the neck 132 to approximately 45 degrees or more for certain surgical procedures where the bent blade provides better access for the procedure. Bending the blade in this manner does not result in the coating 122 flaking or breaking away from the blade body 110, as would occur with thicker coatings and/or less flexible coating materials.

The material of the coating 122 comprises substantially polysiloxane (silicone). Preferably the coating material is a commercially available polysiloxane coating known as "HumiSeal 1C53," which is manufactured and supplied in United States by Chase Corporation of Woodside, N.Y. 11377. The preferred form of this polysiloxane coating is preferably about 60–80 percent of vinylpolydimethylsiloxane and about 5–10 percent polymethylhydrogensiloxane, with the remainder made up of some component which is not known or publicly available to the present inventors. The preferred form of the polysiloxane coating 122 is a relatively fast thermal curing material which begins curing upon its temperature raising to approximately 105 degrees Celsius. Once the curing starts as a result of elevating the temperature above 105 degrees Celsius, the coating material will continue to cure even if the temperature is thereafter reduced. Of course, the amount of time required to achieve adequate curing will vary depending primarily upon the temperature.

The preferred type of polysiloxane coating material is also the type which does not undergo "blooming" as a result of curing the polysiloxane or as a result of the natural aging of the polysiloxane after curing. The hair-like fingers which bloom from the outside surface are therefore not present on the coating 122. Instead, an exterior surface of the coating 122 is substantially smooth. The smooth exterior surface of the coating 122 does not provide an opportunity for the crust-like buildup to adhere to the coating 122, as is typical with other types of blooming polysiloxane coatings used on electrosurgical blades.

The blade body 110 is preferably made of ASTM 304 or 305 stainless steel. An oxide of the iron of the stainless steel of the body 110 is created, and this iron oxide causes the polysiloxane material of the coating 112 to directly adhere to the body 110, without the need for mechanical roughening, primer coats or multiple coats of nonstick, release material. The formation of the iron oxide is discussed below in conjunction with the method of manufacturing the electrosurgical blades 100.

Figure 6:
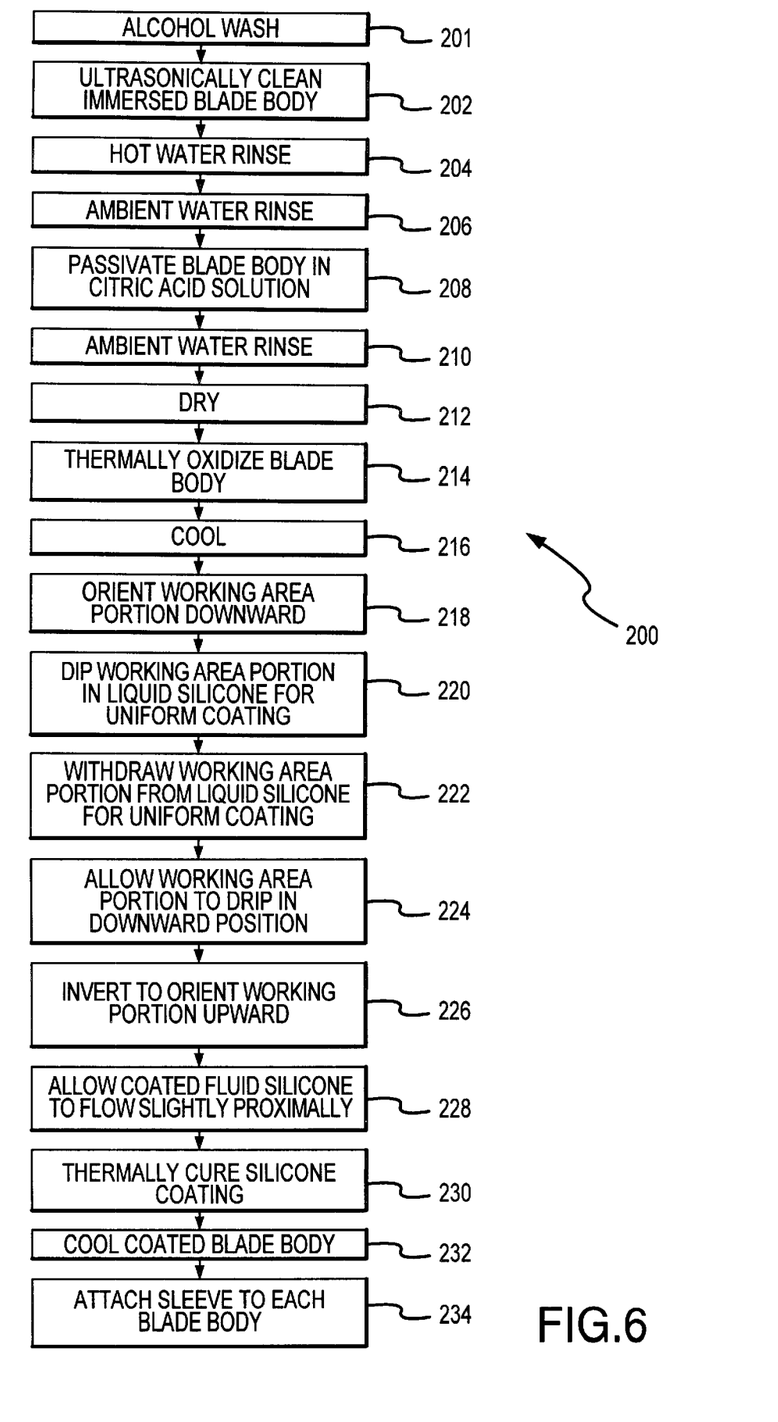
FIG. 6 is a flowchart of the steps involved in manufacturing the electrosurgical blade shown in FIGS. 1–5.

Details concerning a process flow 200 for manufacturing the electrosurgical blade 100 are described in conjunction with FIG. 6. The steps of the process flow 200 shown in FIG. 6 are separately identified by reference numbers. Also, FIG. 6 describes the manufacturing process flow 200 in the context of a single metal body 110 (FIG. 2). In actuality, multiple blade bodies 110 will be treated simultaneously in the process flow 200. Accordingly, the following description of the process flow 200 is stated in terms of treating multiple blade bodies. The steps of the process flow 200 shown in FIG. 6 are applicable to each of the blade bodies as a plurality of the blade bodies are treated simultaneously.

The process flow 200 shown in FIG. 6 begins with a plurality of blade bodies 110 (FIG. 2). The blade bodies 110 have previously been coined or stamped into the typical electrosurgical blade configuration described above, and the blade bodies are typically received in an unclean and non-sterile condition. Some of the initial steps in the process flow 200 are aimed at cleaning the blade bodies to enable the creation of a continuous oxide for good adherence of the polysiloxane coating 122 (FIGS. 4 and 5). The cleaning begins at step 201 by washing the blade bodies in denatured alcohol. The denatured alcohol wash at step 201 removes any grease or other oil substances from the blade bodies to prevent these types of foreign substances from contaminating a cleaning solution in which the blade bodies are ultrasonically cleaned at step 202.

In preparation for ultrasonic cleaning at step 202, the blade bodies are loaded into a rack, fixture or basket so as to enable them to be ultrasonically cleaned. At step 202, the blade bodies 110 are immersed, along with the rack, fixture or basket into which they have been loaded, in a cleaning solution in an ultrasonic cleaning machine. Thereafter the ultrasonic cleaning machine is activated and the blade bodies are ultrasonically cleaned while submerged in the cleaning solution. The ultrasonic energy agitates the cleaning solution to effectively remove particles and substances from the metal bodies. An adequate time duration for the ultrasonic cleaning is approximately 1 to approximately 3 minutes, with approximately a 2 minute cleaning duration preferred. The ultrasonic cleaning accomplished at step 202 is effective in removing many types of particles and substances which may contact or adhere to the blade bodies.

A suitable ultrasonic cleaning machine is a Crest 2800D machine available from Process Equipment & Supply, 31255 Lorain Road, Cleveland, Ohio 44070. The ultrasonic cleaner preferably has a mixture of approximately 20% to approximately 30% RTM 855 detergent booster and approximately 20% to approximately 30% RTM 174 alkaline cleaner, both of which are available from RTM Technologies, P.O. Box 1022, 4284 Ridge Lea Road, Amherst, N.Y. 14226-7022. An amount of de-ionized water about equal to the amount of detergent booster and alkaline cleaner is also added, thereby resulting in a preferred mixture of about 25% RTM 855 detergent booster and about 25% RTM 174 alkaline cleaner and about 50% de-ionized water. The temperature of the cleaning solution is about 122 degrees Fahrenheit, and the de-gas function of the ultrasonic cleaning machine is set for about 9.

After the ultrasonic cleaning at step 202, the blade bodies are subjected to a hot de-ionized water rinse, as shown at step 204. Preferably the hot de-ionized water is at a temperature of approximately 140 degrees Fahrenheit to approximately 160 degrees Fahrenheit, with about 150 degrees Fahrenheit being preferred. The time duration of the hot water rinse at step 204 is about 1 minute. The hot water rinse performed at step 204 adds thermal energy to remove any residual particles that might have been dislodged but not necessarily eliminated from the blade bodies as a result of the ultrasonic cleaning performed at step 202.

Next, as shown at step 206, the blade bodies are then rinsed in ambient or cold de-ionized water, with the temperature of the water at approximately 60 degrees Fahrenheit to approximately 80 degrees Fahrenheit, with a temperature of about 70 degrees Fahrenheit being preferred. The duration of the ambient de-ionized water rinse at step 206 is about thirty seconds. An ambient or cold water rinse may be performed at step 206 to wash away substances that may have been loosened by the hot water rinse at step 204.

De-ionized water is used for the rinsing steps 204 and 206 so as to avoid introducing any foreign matter onto the blade bodies. Tap water might carry such foreign substances, particularly trace metal constituents.

The cleaned blade is then passivated in a citric acid bath as shown at step 208. Suitable citric acid may be Citrisurf 2050, available from Stellar Solutions, 1000 N. Harrison Street, Algonquin, Ill. 60102-2314. The citric acid bath is preferably formed from a concentration of about 33% citric acid and about 67% de-ionized water. One part of this citric acid concentration is thereafter diluted by two parts of de-ionized water to form the citric acid bath in which passivation occurs. The temperature of the citric acid bath is preferably from approximately 125 degrees Fahrenheit to approximately 175 degrees Fahrenheit, and is preferably about 150 degrees Fahrenheit. The time during which the blade bodies are in the citric acid bath is approximately 5 minutes. The time, strength and temperature of the citric acid bath is conventional for cleaning metal parts. Acid other than citric acid could be used to accomplish step 208, but citric acid offers the advantage that it is environmentally compatible.

Next, at step 210, the blade bodies are subjected to an ambient or cold distilled water rinse, at a temperature of approximately 60 degrees Fahrenheit to approximately 80 degrees Fahrenheit, with about 70 degrees Fahrenheit being preferred. The time duration of the distilled water rinse at step 210 is about thirty seconds. The purpose of the rinse at step 210 is to remove any residuals from the citric acid bath at step 208. Since the ultrasonic cleaning step at 208 will have essentially removed any remaining foreign substances from the blade bodies, an ambient or cold water rinse is sufficient to wash those foreign substances away from the blade bodies.

The blade bodies are then dried, as shown at step 212, preferably by directing forced air over the blade bodies at a temperature of about 220 degrees Fahrenheit for about 10 minutes. The time and temperature of the forced air application is not particularly critical so long as the moisture is removed from the blades.

Next, as shown at step 214, the dried blades are then oxidized. Preferably the oxidation is a thermal oxidation accomplished by loading the blade bodies into a high temperature oxidation oven and heating them in an oxygen or air environment at a temperature of about 750 degrees Fahrenheit for about 30 minutes. The temperature in the oxidation oven and the oxygen within the oven causes the iron of the ASTM 304 or 305 stainless steel from which the blade bodies are formed to oxidize into iron oxide. The extent of oxidation and the amount of iron oxide created causes the blade bodies to assume a golden color.

The extent of oxidation is controlled by the temperature of the oxidation oven and the time to which the blade bodies are subjected to that temperature in the oxidation oven. The extent of oxidation is established to be no more than is necessary to achieve the best adherence of the silicone (polysiloxane) coating. The temperature of 750 degrees Fahrenheit for 30 minutes was established empirically for the ASTM 304 and 305 stainless steel, as providing the maximum adherence of the coating directly to the blade bodies. A conventional adherence test of determining the amount of force required to scrape off the silicone coating from the oxidized blade bodies was used to establish maximum adherence oxidation conditions. Less oxidation results in less adherence, and more oxidation also results in less adherence.

The oxidized blade bodies are thereafter cooled at step 216. The cooling results from placing the blade bodies in a clean environment at normal room temperature. The cooling step 216 should be sufficient to cause the blade bodies to reach normal room temperature.

Next, at step 218, the cooled and oxidized blade bodies are oriented with their working area portions 112 (FIG. 3) extending in a vertically downward position. In this position the shank portions 124 are extending vertically upward. In other words, each blade body 110 (FIG. 3) extends vertically, with its shank portion 124 on the top and its working area portion 112 on the bottom. Preferably the orientation step 218 is achieved by loading the blade bodies into a holding or retaining fixture and then orienting the retaining fixture. When loaded into the retaining fixture, the tips 120 of the working area portions 112 are all located in a coplanar relationship. If the blade bodies are loaded into the retaining fixture so that the working area portions 112 of the blade bodies 110 initially point upward, the retaining fixture is thereafter inverted so that the working area portions 112 extend vertically downward.

With the tips 120 of all of the blade bodies oriented in the vertically downward extending direction at step 118, the working area portions 112 blade bodies are thereafter dipped into a pool of the liquid silicone coating material, as shown at step 220. The dipping step 220 involves inserting the working area portions 112 of the blade bodies into the pool of liquid silicone coating material, by moving the blade bodies vertically downward in a direction parallel to the downward extending working area portions 112 at a controlled rate of immersion. The controlled rate of immersion should be selected to result in as uniform of a cross-sectional coating as is possible. Because the tips 120 of all of the blade bodies are located in the same plane when positioned in the retaining fixture, all of the blade bodies are dipped to the same depth in the pool of liquid silicone coating material (approximately to the distal end of the working area portion 112), and all of the blade bodies are coated in the same uniform manner, to the same extent and to the same depth. The substantially immersed working area portion 112 remains in the silicone material for approximately 5 to approximately 7 seconds, with about 6 seconds being preferred. Maintaining the working area portion 112 immersed in the silicone during this time period allows the liquid silicone material to adhere to the greatest extent possible on the oxidized blade body.

The working area portions 112 of the blade bodies 110 are thereafter removed or withdrawn from the liquid silicone material, also at a controlled rate to establish, maintain and promote the uniform coating, as shown at step 222. The working area portions are withdrawn vertically from the pool of liquid silicone material in the opposite direction compared to the direction that the working area portions were inserted into the pool of liquid silicone material. Both the insertion motion and the withdrawal motion are purely direct linear motions without any other associated substantial component of motion.

Next, as shown at step 224, after the working area portions 112 have been withdrawn at step 222, the blade bodies are suspended above the liquid silicone coating material to allow any excess liquid silicone material to drip from the working area portions 112. The blade bodies are suspended in a vertical orientation with the working area portions 112 pointed downward. The liquid silicone material on the working area portions drains downward toward the tip 120, and the excess liquid drips from the tips back into the pool of liquid silicone material. Allowing the excess liquid silicone material to drain by gravity downward and drip off of the tips 120 reduces the thickness of the uniform cross-sectional layer of coating material. Preferably, the blade bodies are permitted to drip in this manner for approximately 15 to approximately 20 seconds, with about 17 seconds being preferred.

The blade bodies are then inverted as shown at step 226. Inverting the blade bodies involves slowly rotating the blade bodies in a vertical plane about a horizontal axis to cause the working area portions 112 to point vertically upward and the shank portions 124 to point vertically downward. The inversion of the blades at step 226 is gentle enough to avoid any distortion or nonuniformity in the coating of silicon material established at steps 220, 222 and 224. The coated blades are maintained in the inverted orientation established at step 226 for approximately 50 to approximately 70 seconds, with 60 seconds being the preferred time.

Orienting the blades in the inverted manner at step 226 causes the coating material to withdraw uniformly away from the distal tip 120 of the working area portion and move toward the proximal end of the working area portion, as shown at step 228. As a consequence, the uniform cross-sectional thickness of the coating near the distal tip 120 is somewhat thinner than the uniform cross-sectional thickness of the coating near the middle location of the working area portion 112, as shown in FIG. 5. The inversion at step 126 causes the coating 122 to have the linearly-increasing thickness, with the uniform thickness being the least near the tip 120 and the greatest at middle locations of the working area portion 112. Generally speaking, between the middle location of the working area portion (approximately point 144, FIG. 5) and the distal location of the working area portion, the uniform cross-sectional thickness of the coating 122 may remain approximately the same as at point 144 or may even slightly decrease in thickness.

Figure 3:
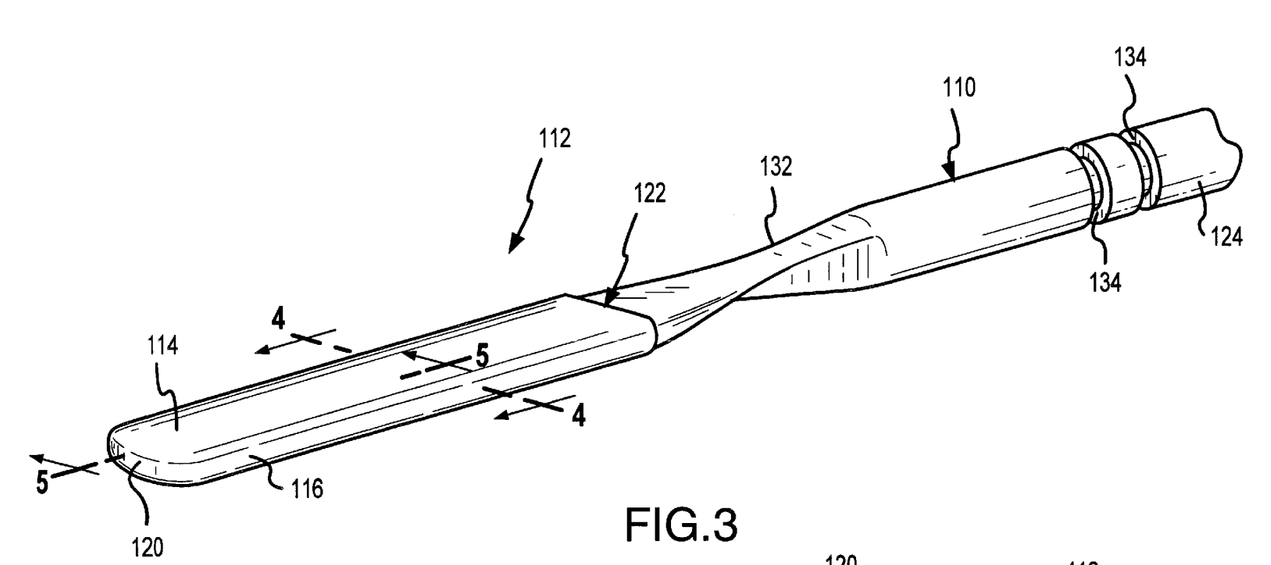
FIG. 3 is an enlarged perspective view of a distal end working area portion of a blade body of the the electrosurgical blade shown in FIGS. 1 and 2.

Because of the dripping permitted at step 220, any excess amount of the liquid silicone coating material generally does not flow past the neck area 132 of the blade body 110 (FIGS. 1, 2 and 3). However, should such excess material flow past the neck area 132, the grooves 134 are available to receive and contain that excess material before it flows onto the hub 128 or onto the exposed end 126 of the shank portion 124 (FIG. 1). Thus, the grooves 134 provide an extra reservoir to collect any excess silicone material and prevent it from coating parts of the electrosurgical blade 100 which are not intended to be coated.

The coated working area portions 112 of the blade bodies 110 are then cured, as shown at step 230. Since the liquid silicone material is a thermal curing substance, the curing is achieved by subjecting the liquid silicone material to heat. The particular type of liquid silicone material preferred, HumiSeal 1C53, commences curing when its temperature is elevated to greater than 105 degrees Celsius. Once the temperature has been elevated to greater than 105 degrees Celsius, the curing will continue even though the temperature drops below that level. Curing is related to the time at which a temperature is maintained; a higher temperature will result in any shorter curing time, and conversely, a lower temperature will require a longer curing time.

Preferably the curing is accomplished by placing the blade bodies in an infrared (IR) oven. The temperature in the oven is maintained at approximately 400 degrees Fahrenheit to accomplish curing in approximately 3 minutes. This temperature and this amount time has proved adequate for curing the relatively thin and uniform coating of silicone release material on the working area portions 112 of the blade bodies. While convection heating may also be used to cure the coating, it has been discovered that infrared curing appears to cure the material more uniformly. The infrared curing also appears to cause a smoother or slicker release surface of the coating 122. Curing as a result of the infrared radiation also occurs more quickly than with convection heating.

Thereafter, at step 232, the coated metal bodies 112 are removed from the IR oven and are allowed to cool to room temperature. Because the silicone coating material is of the type which does not bloom hair-like fingers from the outer surface, the outer surface of the coating 122 is generally smooth. Moreover, the non-blooming characteristics of the silicone coating material do not result in the hair-like fingers blooming at some time after the coating has been cured.

After cooling, the hub 128 (FIGS. 1 and 2) is inserted over each shank portion 124 of the blade body 110, to complete the manufacture of the electrosurgical blade 100. The step of attaching the hub to the blade body is shown at step 234. If necessary because the liquid coating material has drained past the concentric grooves 134 (FIGS. 1 and 2) and onto the shank portion 124, the coating material 122 may be scraped off of the shank portion 124 before inserting the hub 128 onto the shank portion. The hub is preferably attached by press fitting the shank portion into its center opening 130.

The resulting nonstick, release coating material comprising substantially polysiloxane (silicone) preferably has the dimensions and characteristics previously described. The thin cross-sectionally uniform coating 122 provides adequate nonstick and release characteristics to inhibit the accumulation of the crust-like buildup. The uniform cross-sectional coating 122 also provides adequate thermal and electrical impedance to inhibit the buildup of crust-like material. Moreover, because of the relatively thin and uniform cross-sectional characteristics of the coating, less drag is created when cutting with the electrosurgical blade 100 compared to thicker and non-uniform coatings on other types of electrosurgical blades, thereby possibly facilitating a better "feel" of the blade to the surgeon. It is believed that the thin uniform coating 122 of the cured silicone material has viscosity characteristics so that in the event that an arc passes through it, the silicone material will tend to flow to close or attempt to close any hole or separation formed in the silicone material by the arc.

The oxidation of the electrosurgical blade 110 is believed to provide an adequate and uniform surface by which to anchor the silicone coating 122, while providing a uniform field across the broad side 114 of the working area portion 112. Grit blasting or other mechanical roughening of the surface is not required to achieve adequate adherence of the coating 122. An excessive thickness of the release material is not required to electrically insulate the point source field gradients caused by the mechanically roughened peaks in the metal body. In addition, the requirement and necessity to place primer materials and multiple coatings on the blade body is avoided, thereby simplifying the cost and effort to manufacture the electrosurgical blade 100. Many other advantages and improvements will be apparent upon gaining a full appreciation for the present invention.

While this invention has been described in the specification and illustrated in the drawings with reference to a preferred embodiment, various changes or modifications may be made without departing from the scope of the claims. Therefore, it is intended that the invention not necessarily be limited to the particular embodiment and details disclosed in the specification and shown in the drawings, but that the invention will include all embodiments, modifications and changes as may come within the scope of the following claims.

The invention claimed is:

1. An electrosurgical active electrode used for conducting electrical energy to tissue during an electrosurgical procedure comprising:

a conductive metallic body having a working area portion and a connection end to which the electrical energy is conducted, the working area portion of the body including at least one broad non-roughened side which has been oxidized; and     a nonstick release coating comprising substantially polysiloxane directly adhered to the oxidized broad side of the body, the nonstick release coating having a substantially uniform cross-sectional thickness extending transversely of the working area portion.

2. An electrosurgical active electrode as defined in claim 1 wherein:

the broad side is thermally oxidized.

3. An electrosurgical active electrode as defined in claim 1 wherein:

the metallic body is formed of stainless steel;

the stainless steel of the metallic body contains iron; and     the oxidation of the broad side is iron oxide.

4. An electrosurgical active electrode as defined in claim 3 wherein:

the iron oxide is formed by thermally heating the metallic body in an oxygen containing atmosphere.

5. An electrosurgical active electrode as defined in claim 1 wherein:

the substantial polysiloxane of the nonstick release coating contains 60–80 percent of vinylpolydimethylsiloxane.

6. An electrosurgical active electrode as defined in claim 5 wherein:

the substantial polysiloxane of the release coating further contains 5–10 percent polymethylhydrogensiloxane.

7. An electrosurgical active electrode as defined in claim 1 wherein:

the substantial polysiloxane of the release coating contains 5–10 percent polymethylhydrogensiloxane.

8. An electrosurgical active electrode as defined in claim 1 wherein:

the substantial polysiloxane of the release coating is thermally cured.

9. An electrosurgical active electrode as defined in claim 1 wherein:

the substantial polysiloxane of the release coating does not bloom hair-like fingers.

10. An electrosurgical active electrode as defined in claim 1 wherein:

the broad side of the working area portion extends substantially longitudinally of the body; and     the substantially uniform thickness of the coating extends substantially transversely with respect to the longitudinally extending broad side.

11. An electrosurgical active electrode as defined in claim 10 wherein:

the thickness of the substantially uniform coating changes approximately linearly along the longitudinal length of the broad side.

12. An electrosurgical active electrode as defined in claim 11 wherein:
the broad side extends from a distal tip of the working area portion to a location spaced proximally of the distal tip; and
the thickness of the substantially uniform coating is less at the distal tip than at the location spaced proximally of the distal tip.

13. An electrosurgical active electrode as defined in claim 1 wherein:
the coating is a single layer coating formed by dipping.

14. An electrosurgical active electrode as defined in claim 1 wherein:
the body includes a shank portion connected to the working area portion by a neck area; and
the body further includes at least one groove formed in a shank portion adjacent to the neck area in which to receive and contain excess liquid coating material applied to the body.

15. An electrosurgical active electrode as defined in claim 1 wherein:
the broad side is substantially smooth and free of mechanical roughening.

16. An electrosurgical active electrode as defined in claim 1 wherein:
the working area portion has a substantial rectangular cross-sectional configuration having two of the longitudinally extending broad sides and two relatively narrower longitudinally extending edges joining the broad sides at longitudinally extending corners;
each broad side is substantially smooth and free of mechanical roughening;
the metallic body is formed of stainless steel which contains iron;
both broad sides of the working area are oxidized as iron oxide formed by thermally heating the stainless steel body in an oxygen-containing atmosphere;
the uniform coating is directly adhered to both broad oxidized sides;
the substantial polysiloxane is thermally cured and does not bloom hair-like fingers and contains 60–80 percent of vinylpolydimethylsiloxane and 510 percent polymethylhydrogensiloxane; and
the substantially uniform thickness of the coating extends substantially transversely from one corner to the other corner of each broad side.

17. An electrosurgical active electrode as defined in claim 16 wherein:
each broad side extends from a distal tip of the working area portion to a location spaced proximally of the distal tip; and
the thickness of the substantially uniform coating increases approximately linearly along the length of each broad side from the distal tip to the location spaced proximally of the distal tip.

18. A method of manufacturing a coated electrosurgical active electrode from a conductive metallic body having a working area portion including at least one broad side having smooth and non-roughened characteristics and also having a connection end to which electrical energy is conducted when the active electrode is used in electrosurgery, comprising the steps of:
oxidizing an element of the metallic body over the broad side;
coating the oxidized broad side to a uniform cross-sectional thickness with a liquid nonstick release material containing substantially polysiloxane; and
curing the polysiloxane of the material.

19. A method as defined in claim 18 further comprising the step of:
dipping the oxidized broad side into the liquid material at a controlled rate to create the uniform coating.

20. A method as defined in claim 19 further comprising the step of:
inserting the broad side into the pool and withdrawing the broad side from the pool once before curing the polysiloxane.

21. A method as defined in claim 20 further comprising the step of:
inverting the broad side to extend vertically upward after withdrawing the broad side from the pool of liquid material.

22. A method as defined in claim 20 further comprising the step of:
maintaining the vertical orientation of the broad side after withdrawing the broad side from the pool of liquid material to allow excess liquid material on the broad side to drip from the broad side before inverting the broad side to extend vertically upward.

23. A method as defined in claim 22 wherein the metallic body further includes a shank portion extending from the working area portion, and the method further comprises the step of:
positioning a hub of electrically insulating material over the shank portion from an end of the shank portion opposite the working area portion.

24. A method as defined in claim 23 wherein the metallic body is stainless steel and the element is iron, and the method further comprises the step of:
thermally oxidizing iron at the surface of the metallic body into iron oxide.

25. A method as defined in claim 24 further comprising the step of:
thermally oxidizing the iron until the surface of the metallic body assumes a golden color.

26. A method as defined in claim 20 wherein each broad side extends from a distal tip of the working area portion to a location spaced proximally of the distal tip and the method further comprises the steps of:
maintaining the inverted position of the broad side extending vertically upward to allow liquid material on the broad side to move away from the tip toward the location spaced proximally of the distal tip until a thickness of the substantially uniform coating increases approximately linearly along the length of the broad side from the distal tip to the location spaced proximally of the distal tip; and
curing the polysiloxane after the approximately near increase in thickness along the length of the broad side from the distal tip to the location spaced proximally of the distal tip has been established.

27. A method as defined in claim 18 wherein the broad side of the working area portion extends substantially longitudinally along the metallic body and said method further comprises the steps of:
vertically orienting the longitudinally extending broad side to extend downward; and
vertically inserting downwardly the vertically oriented broad side into a pool of the liquid material at a controlled rate; and vertically withdrawing upwardly the vertically oriented broad side from the pool of the liquid material at a controlled rate after inserting the broad side.

28. A method as defined in claim 18 further comprising the step of:

heating the metallic body in an ambient environment containing oxygen to oxidize the element of the metallic body.

29. A method as defined in claim 25 wherein the stainless steel is one of ASTM 304 or ASTM 305.

30. A method as defined in claim 18 further comprising the step of:

thermally oxidizing the surface of the metallic body to a predetermined extent to obtain substantially maximum adherence of the cured polysiloxane to the oxidized broad side.

31. A method as defined in claim 30 further comprising the step of:

avoiding blooming of hair-like fingers from the release material by a release material containing substantially polysiloxane for use which does not bloom hair-like fingers.

32. A method as defined in claim 31 further comprising the step of:

placing the metallic body in citric acid to passivate the metallic body.

33. A method as defined in claim 31 further comprising the step of:

cleaning the metallic body prior to passivating the metallic body.

34. A method as defined in claim 32 further comprising the step of:

cleaning the metallic body by submerged in the metallic body in a cleaning fluid and ultrasonically agitating the cleaning fluid and the submerged metal body.

35. A method as defined in claim 18 further comprising the steps of:

using a thermally curing liquid nonstick release material containing substantially polysiloxane with which to uniformly coat the oxidized broad side; and thermally curing the polysiloxane of the material.

36. A method as defined in claim 18 further comprising the step of:

passivating the metallic body prior to the steps of oxidizing, coating and curing.

* * * * *